United States Patent
Boileau

(10) Patent No.: US 7,399,466 B2
(45) Date of Patent: *Jul. 15, 2008

(54) METHOD AND COMPOSITIONS FOR PROMOTING OSTEOGENESIS

(75) Inventor: Guy Boileau, Quebec (CA)

(73) Assignee: Enobia Pharma Inc. (CA)

( * ) Notice: Subject to any disclaimer, the term of this patent is extended or adjusted under 35 U.S.C. 154(b) by 252 days.

This patent is subject to a terminal disclaimer.

(21) Appl. No.: 10/362,259

(22) PCT Filed: Aug. 23, 2001

(86) PCT No.: PCT/CA01/01220

§ 371 (c)(1),
(2), (4) Date: Jul. 29, 2003

(87) PCT Pub. No.: WO02/15918

PCT Pub. Date: Feb. 28, 2002

(65) Prior Publication Data

US 2005/0069569 A1    Mar. 31, 2005

Related U.S. Application Data

(60) Provisional application No. 60/227,012, filed on Aug. 23, 2000.

(51) Int. Cl.
*A61K 38/48* (2006.01)
*A61F 2/02* (2006.01)
*C12N 9/64* (2006.01)
*C12N 15/62* (2006.01)
*C12N 15/79* (2006.01)

(52) U.S. Cl. .............. 424/94.67; 424/423; 424/435; 424/484; 435/69.1; 435/69.7; 435/226; 435/252.3; 435/320.1

(58) Field of Classification Search .............. None
See application file for complete search history.

(56) References Cited

U.S. PATENT DOCUMENTS 5,208,219 A * 5/1993 Ogawa et al. .................. 514/12

(Continued)

FOREIGN PATENT DOCUMENTS

DE    40 08 546 A    9/1990

(Continued)

OTHER PUBLICATIONS

A. Faimey et al.; "Abnormal osteocalcin binding in rheumatoid arthritis," 1990; Animals of the Rheumatic Diseases; vol. 49, pp. 229-230.

(Continued)

*Primary Examiner*—Nashaat T. Nashed
*Assistant Examiner*—William W. Moore
(74) *Attorney, Agent, or Firm*—DLA Piper US LLP

(57) ABSTRACT

The object of the present invention is to increase PHEX activity to improve the osteogenic process in a mammal where this process has been diminished due to pathology or a condition that require osteogenesis. Osteocalcin is an endogenous inhibitor of the PHEX activity. Therefore, the identification of a substance capable of potentiating PHEX activity by preventing the inhibitory action of endogenous inhibitors will improve osteogenesis. Since PHEX is generally associated with the growth plane of bone or teeth and the absence of osteocalcin is associated with increased bone mass, potentiation of PHEX activity can promote bone growth. Increased PHEX activity can also be obtained by administration of the enzyme itself.

22 Claims, 7 Drawing Sheets

U.S. PATENT DOCUMENTS

| | | | | |
|---|---|---|---|---|
| 5,413,989 | A | * | 5/1995 | Ogawa et al. ............... 514/12 |
| 6,787,644 | B1 | * | 9/2004 | Cerretti .................... 536/23.2 |
| 6,790,649 | B1 | * | 9/2004 | Crine et al. ................ 435/212 |
| 6,881,404 | B2 | * | 4/2005 | Boodhoo et al. ......... 424/94.67 |

FOREIGN PATENT DOCUMENTS

| | | |
|---|---|---|
| EP | 0 504 423 A | 9/1992 |
| EP | 0 834 740 A | 4/1998 |
| WO | 98 10078 A | 3/1998 |
| WO | 00 50580 | 8/2000 |

OTHER PUBLICATIONS

Guy Boileau et al, "Characterization of PHEX endopeptidase catalytic activity: Identification of parathyroid-hormone-related peptide107-139 as a susbstrate and osteocalcin, PPi and phosphate as inhibitors." *Biochemical Journal*, vol. 355, No. 3, May 1, 2001, pp. 707-713.

Yves Sabbagh et al.: "Disease-causing missense mutations in the PHEX gene interfere with membrance targeting of the recombinant protein" *Human Molecular Genetics*, vol. 10, No. 15, 2001, pp. 1539-1546.

Galia Ghaddar et al., "Molecular cloning and biochemical characterization of a new mouse testis soluble-zinc-metallopeptidase of the neprilysin family", *Biochemical Journal*, vol. 347, No. 2, Apr. 15, 2000, pp. 419-429.

Laurent Beck et al., "Pex/PEX tissue distribution and evidence for a deletion in the 3' region of the Pex gene in X-linked Hypophosphatemic mice." *Journal of Clinical Investigation*, vol. 99, No. 6, 1997, pp. 1200-1209.

P.S.N. Rowe, "The Role Of The Phex Gene (PEX) In Families With X-Linked Hypophosphataemic Rickets" *Current Opinion In Nephrology and Hypertension, Rapid Science*, vol. 7, No. 4, 1998, pp. 367-376.

Kiyono, et al., Partial Translation of Research Report, Abstract only, one page.

* cited by examiner

Figure 4

PTHrP(107-139): TRSAWLDSGVTGSGLEGDHLSDTSTTSLELDSR
Fragments: (107-112) TRSAWL
(107-127) TRSAWLDSGVTGSGLEGDHLS
(128-136) DTSTTSLEL
(128-139) DTSTTSLELDSR

METHOD AND COMPOSITIONS FOR PROMOTING OSTEOGENESIS

CROSS REFERENCE TO RELATED APPLICATIONS

This application is a §371 of International Application No. PCT/CA01/01220, with an inter-national filing date of Aug. 23, 2001 (WO 02/15918, published Feb. 28, 2002 in English under PCT Article 21(2)), which claims priority of U.S. Provisional Application No. 60/227,012, filed on Aug. 23, 2000. All documents above are herein incorporated by reference.

FIELD OF THE INVENTION

The present invention relates to a novel process for promoting the osteogenic process, the deficiency of which is attributable to various pathologies. More specifically, the present invention is focused on the enhancement of osteogenesis by increasing the activity of PHEX, either by administering PHEX or by increasing the activity of existing PHEX by inhibiting osteocalcin. The present invention further provides a method for screening agents capable of abolishing the inhibitory action of osteocalcin.

BACKGROUND OF THE INVENTION

The bone. The solid matrix of the bone is made of an organic phase, collagen, and of an inorganic phase, composed of calcium and phosphate (hydroxyapatite). Bones are continuously remodeling themselves, a process of combined dissolution (resorbtion) and re-construction of the bone matrix. The bone relies on two cell types for remodeling process: osteoclasts, which are responsible for resorbtion, and osteoblasts, which promote for bone formation. In normal bones, both processes are strictly coordinated to maintain bone mass within defined limits. More specifically, at a specific site, resorbtion occurs first and over a shorter period than bone formation. At the end of the formation stage most osteoblasts will disappear through the apoptotic process. About 10% will be enclosed in the bone and remain there to form osteocytes. It is generally believed that the osteocytes participate in some form of mechanical stress sensing mechanism. Osteoporosis occurs when the resorbtion process is initiated more often than formation is completed, leading progressively to more fragile bones (Harisson 14th Ed). PHEX. The PHEX gene (formerly PEX; a Phosphate regulating gene with homologies to Endopeptidases on the X chromosome) was identified by a positional cloning approach as the candidate gene for human X-linked hypophosphatemia (XLH) (1). XLH is a Mendelian disorder of phosphate homeostasis characterized by growth retardation, rachitic and osteomalacic bone disease, hypophosphatemia, and renal defects in phosphate re-absorption and vitamin D metabolism (2). Several groups have cloned and sequenced the human and mouse PHEX/Phex cDNAs (3-7) (PHEX/Phex refers to the human and mouse genes, respectively). Amino acid sequence comparisons have demonstrated homologies between PHEX/Phex protein and members of the M13 endopeptidase family, as previously observed in the partial sequence of the candidate gene (1). The M13 endopeptidases are zinc-containing type 11 integral membrane glycoproteins with a relatively short cytoplasmic amino-terminal region, a single transmembrane domain, and a long extracytoplasmic domain, which contains the active site of the enzyme (8). In addition to PHEX, this family includes neprilysin (NEP, neutral endopeptidase 24.11), a widely distributed peptidase involved in the degradation of several bioactive peptides (9), the endothelin-converting enzymes 1 and 2 (ECE-1 and ECE-2) responsible for the processing of inactive big-endothelins into active endothelins (10), the Kell blood group protein, a protein of the erythrocyte membrane with unknown function (11), and ECEL/DINE (12,13) and SEP/NL1 (14,15), two recently reported peptidases with homology to the neprilysin family.

The precise physiological role of PHEX is unknown and the mechanisms whereby loss of PHEX function causes renal phosphate wasting, abnormal regulation of vitamin D metabolism and impaired bone mineralization are not completely understood. Homology of PHEX to members of the M13 family of zinc metallopeptidases suggests a role in regulating the activity of extra-cellular bioactive peptide(s) that act in an autocrine, paracrine or endocrine fashion. In support of this hypothesis, Lajeunesse et al. (16) and Nesbitt et al. (17) have reported the existence of a renal phosphate transport inhibitory factor in the culture medium of osteoblasts isolated from the Hyp mouse, an animal model for human XLH (18). The role of PHEX would appear be to inactivate this circulating factor. However, the molecular identity of this factor (phosphatonin) has yet to be established.

PHEX and mineralization. In situ hybridization performed on sections of embryos and newborn mice showed the presence of Phex mRNA in osteoblasts and odontoblasts (32). Phex gene expression was detectable on day 15 of embryonic development, which coincides with the beginning of intracellular matrix deposition in bones. Moreover, Northern analysis of total RNA from calvariae and teeth of 3-day-old and adult mice showed that the abundance of the Phex transcript is decreased in adult bones and in non growing teeth but maintained in growing incisors throughout life. This result was confirmed when the presence of the Phex protein in new born and adult bones was investigated by Western blotting using a monoclonal antibody raised against human PHEX. Immunohistochemical studies on a 2 month-old mouse showed exclusive labeling of mature osteoblasts and osteocytes in bones and of odontoblasts in teeth (27). Taken together these results suggest that PEX/Phex plays an important role in the development and maintenance of mineralization in these tissues.

Studies performed with the Hyp mouse, an animal model harboring a large deletion in the 3' region of the Phex gene (5) and exhibiting the same phenotypic features that characterize patients with XLH (18), also suggest that PHEX is involved, in an unknown way, in the mineralization process. Hyp mice exhibit enlarged osteoid area in bones (27, 33) which was shown not to be due to abnormal matrix deposition (34,35) but to impaired mineralization (33).

Osteocalcin. Osteocalcin is the most abundant of the non-collagenous bone proteins and is expressed only in osteoblasts. The mature peptide is 49 amino acids long with 3 Gla residues and one difulfide bond. A vitamin K-dependent gamma-carboxylase is responsible for the transformation of certain Glu into Gla residues. These Gla residues are well known for their affinity toward calcium ions and hydroxyapatite crystals. About 80% of bone mass is made-up of hydroxyapatite, a mineral composed of calcium and phosphate. An increase in osteocalcin mRNA is associated with the mineralization stage and the transformation of osteoblasts into osteocytes (39).

In vitro, osteocalcin inhibits growth of mineral crystals (36, 37) whereas in vivo, gene targeting aimed at the disruption of both mouse osteocalcin genes resulted in the generation of osteocalcin-deficient animals (38). These osteocalcin-knockout mutant mice display a phenotype "opposed to osteoporosis" which is also characterized by an increase in the rate of bone formation, increased bone mass, as well as an overall improved functional quality of the bone.

SUMMARY OF THE INVENTION

As suggested above, PHEX activity is required for proper bone formation. Unexpectedly, osteocalcin was found to inhibit the enzymatic activity of PHEX in vitro. An object of the present invention is to increase in vivo PHEX activity to improve bone characteristics, either by reducing the inhibitory activity of osteocalcin or through the administration of PHEX. The present invention further provides a method for identifying agents capable of increasing (potentiating) PHEX activity by preventing the inhibitory activity of osteocalcin on PHEX. The present invention also provides for improved means of PHEX production and purification as well as for a method of increasing PHEX activity by administering soluble PHEX enzyme by means of injection, gene therapy, where the therapeutic gene codes for the soluble protein, or alternatively, with cell therapy, where the therapeutic cell produce the soluble protein.

More specifically, the present invention combines the inhibitory capacity of osteocalcin on PHEX activity with the invention disclosed in International Application Number PCT/CA00/00201 (hereinafter referred to as the "201 method"), to identify agents capable of increasing significantly PHEX activity. The 201 method provides for the necessary reagents and for the measurement of PHEX activity. The present invention uses the 201 method in the presence of osteocalcin to screen agents capable of abolishing the inhibitory action of osteocalcin. Consequently, when osteocalcin inhibitory activity is reduced, PHEX enzymatic activity is increased (or potentiated). To this end, various reagents were prepared and tools designed to construct an enzymatic assay. Several improvements to the 201 method are described herein. These improvements include the use of a new vector to produce secPHEX and the use of a hydrophobic column as a second purification step to obtain PHEX having a greater purity. The new vector contains a NL1-PHEX fusion constructed in such fashion that PHEX sequences are immediately downstream from the NL1 furin cleavage site. NL1 is a peptidase secreted by cells due to a furin-cleavage site (42) in its extracellular domain (15). Upon biosynthesis of the fusion protein, PHEX is secreted due to furin cleavage. The advantage of this system over the one described in the 201 method is that no exogenous amino acid residue is present at the N-terminus of secPHEX.

PHEX enzymatic activity can also be potentiated with the administration of the soluble form of the enzyme as provided in the 201 method and in the improvements herein. Moreover, PHEX enzymatic activity can be potentiated with the administration of the soluble form of the inactive enzyme, as provided herein, where the inactive PHEX (iPHEX) acts as a decoy to bind osteocalcin and thereby reduces the free concentration of osteocalcin. Similarly, osteocalcin activity can be reduced with an antibody prepared in such a way to prevent the binding of osteocalcin to PHEX.

In addition, the present invention provides several new substrates necessary for the measurement of the enzymatic activity of PHEX. Another improvement involves the use of a PHEX substrate with a single cleavage site. This simplifies the calculations required to measure the activity of the enzyme. The PHEX substrate can be selected from the following permutations: any peptides selected from the sequence represented by human PTHrP 107-139 (SEQ ID NO: 4) where the selected peptide comprises at least 2 but preferably 4 residues on each side of at least one DT or DS amino acid pair. Any selection can be further modified with conservative amino acid substitutions: any hydrophobic amino acid can be replaced by another hydrophobic acid, any acidic amino acid can be replaced by another acidic amino acid, any basic amino acid can be replaced by another basic amino acid, serine can be replaced by threonine and vice versa, asparagine can be replaced by glutamine and vice versa. A person skilled in the art will recognize that amino acid substitutions should be made in such a way that the enzymatic process will not be adversely interfered with, in particular with substitutions that involve proline or glycine. One example of a substrate is AWLDSGV (SEQ ID NO: 1) corresponding to human PTHrP 110-116.

The present invention also relates to compositions for treating bone-related disorders in humans and animals. The present invention particularly provides for the treatment of reduced bone mass, including its most frequent manifestation, osteopenia, osteoporosis, as well as various forms of rickets, including X-linked hypophosphatemic rickets. Also, the present invention particularly provides for the faster regeneration of bone mass after bone fractures, the implantation of orthopedic prostheses and the implantation of dental prostheses.

DESCRIPTION OF THE SPECIFIC EMBODIMENTS OF THE INVENTION

The invention will now be described with reference to the following specific embodiments and drawings, the purpose of which is to illustrate the invention and not to limit its scope.

A. Schematic representation of PHEX protein (PHEX), and amino acid sequence of the wild-type (TM) and mutated (sec) transmembrane domains (SEQ ID NO: 2 and SEQ ID NO:3, respectively). The hatched box indicates the position of the transmembrane domain and the solid box shows the position of zinc-binding amino acids. Amino acid sequences are presented in the one letter code. In the sec sequence, bold letters show the position of mutated amino acids whereas dashes (−) depict deleted residues.

B. Immunoblot analysis of PHEX, secPHEX and secPHEXE581V expression. Proteins from cellular extracts (c) or culture media (m) of mock-transfected LLC-$PK_1$ cells (Mock) or cells transfected with either PHEX, secPHEX or secPHEXE581V (secPHEXmut) were resolved on a 7.5% SDS-PAGE gel and visualized with a PHEX-specific antibody as described in the Materials and Methods. Some samples were treated with PNGase F (F) or endo H(H) before electrophoresis. (−) refers to untreated samples. The positions of molecular mass markers are indicated (Mr).

Figure 2:
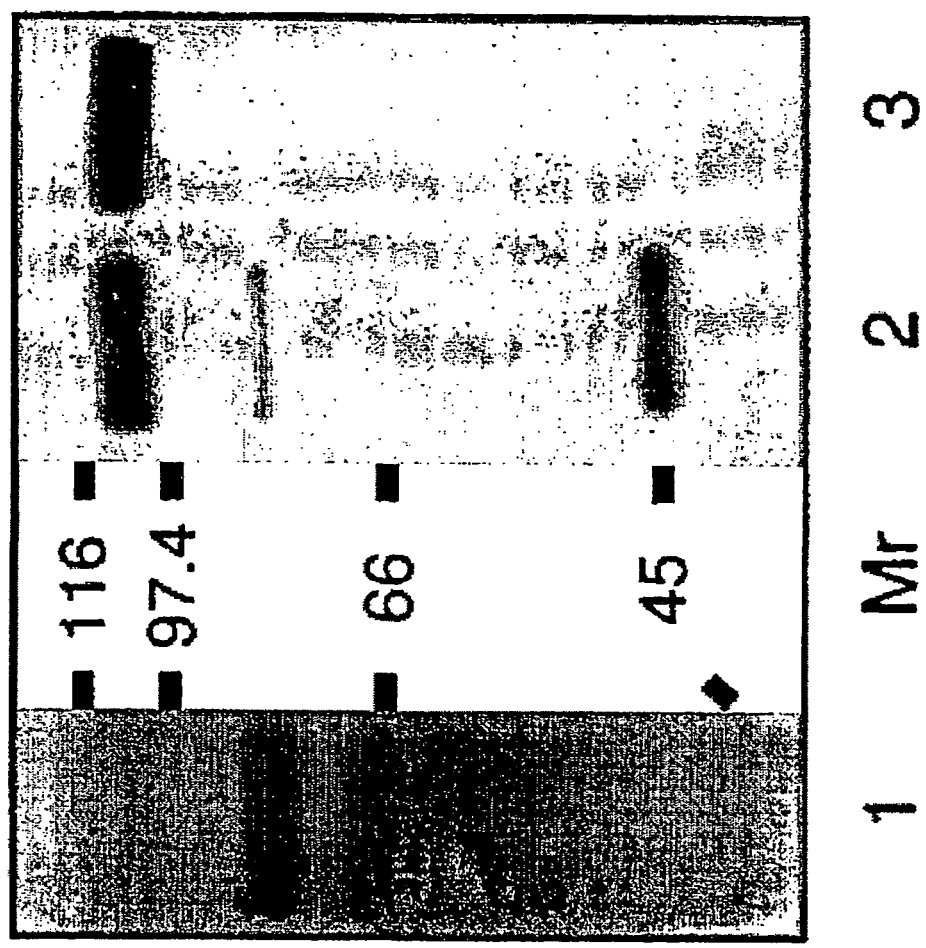

FIG. 2. Purification of secPHEX. Proteins present in the culture medium of secPHEX-producing LLC-$PK_1$ cells (lane 1), or in fractions pooled after the SP-Sepharose column (lane 2) or after the Butyl Sepharose 4 column (lane 3) were separated on a 7.5% acrylamide gel and silver stained. The positions of molecular mass markers are indicated (Mr).

Figure 3:
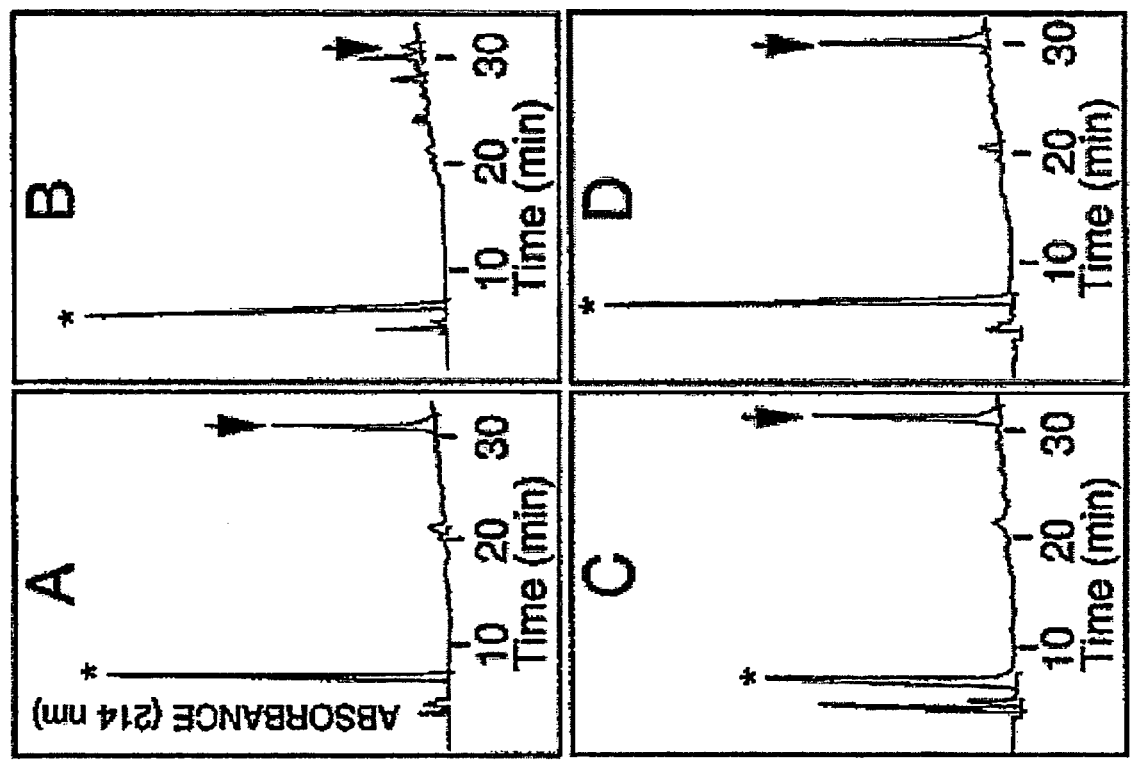

FIG. 3. secPHEX activity. HPLC analysis of $PTHrP_{107-139}$ digestion fragments. (A) $PTHrP_{107-139}$ in the absence of secPHEX; (B) $PTHrP_{107-139}$ in presence of secPHEX; (C) $PTHrP_{107-139}$ in the presence of secPHEX and 1 mM EDTA; (D) $PTHrP_{107-139}$ in the presence of secPHEXE581V. Arrows indicate the elution position of $PTHrP_{107-139}$ and asterisks the elution position of Tyr-Gly-Gly used as internal standard.

FIG. 4. Identification of secPHEX cleavage positions in PTHrP$_{107-139}$. The sequences of PTHrP$_{107-139}$, and fragments identified by mass spectrometry are presented (SEQ ID NO: 4 to SEQ ID NO:8). Cleavage sites are indicated by arrows. The one letter code is used to represent the amino acid residues.

Figure 5:
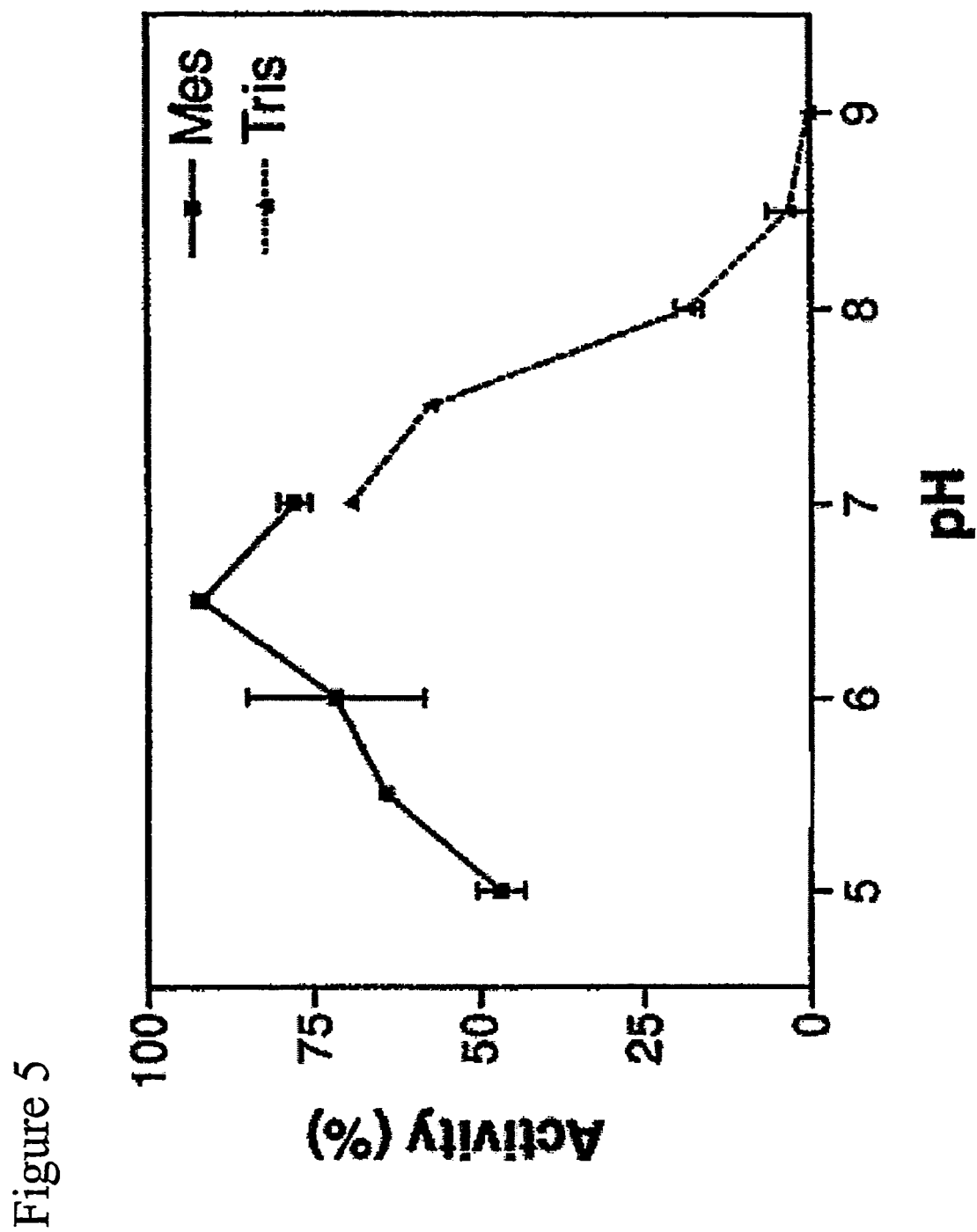

FIG. 5. pH dependency of secPHEX activity. secPHEX and PTHrP$_{107-139}$ were incubated in different pH conditions as described in the text and the extent of hydrolysis of the substrate determined by HPLC. The condition yielding the highest hydrolysis was arbitrarily set at 100%. Squares: assays performed in MES buffer; triangles: assays performed in Tris buffer.

Figure 6:
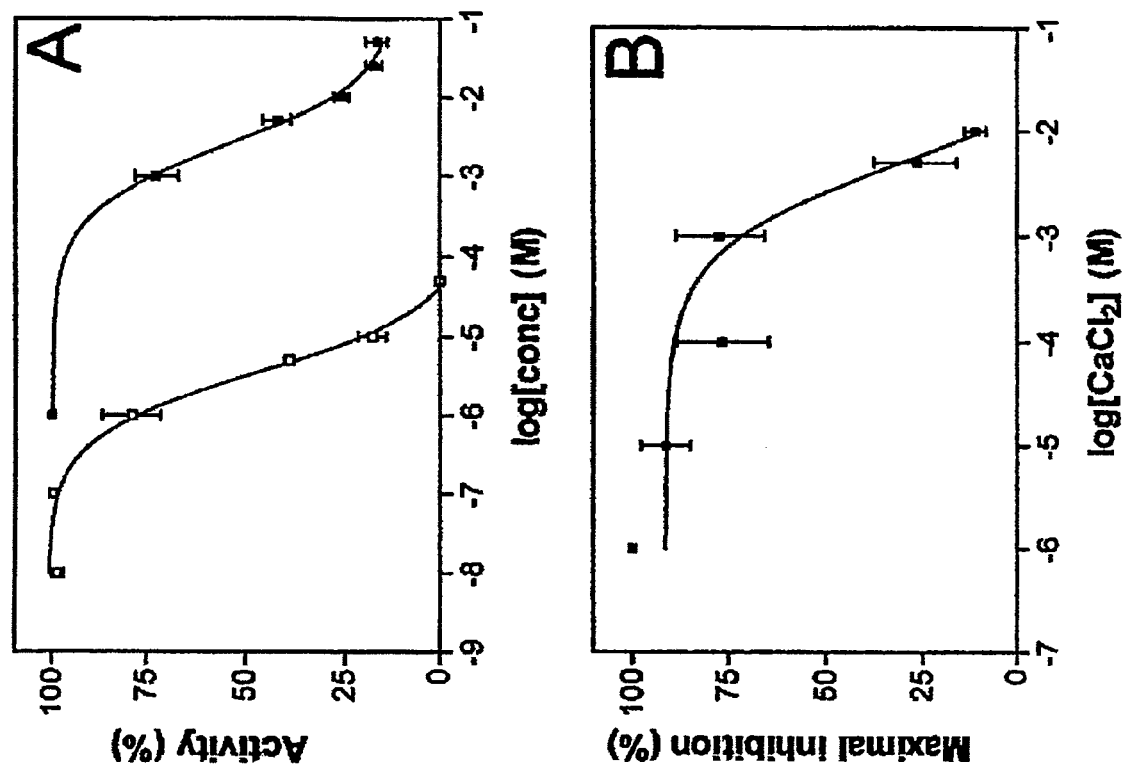

FIG. 6. Effects of increasing concentrations of pyrophosphate, osteocalcin, and calcium in the presence of osteocalcin on PTHrP$_{107-139}$ degradation by purified secPHEX. secPHEX activity was measured in the presence of increasing concentrations of pyrophosphate or osteocalcin (A), and CaCl$_2$ (B)(with a constant osteocalcin concentration of $2\times10^{-6}$M). In (A) 100% corresponds to the activity of secPHEX in the absence of inhibitors. In (B), osteocalcin inhibitory potency is measured and 100% corresponds to the inhibition observed in the presence of $2\times10^{-6}$M osteocalcin and the absence of CaCl$_2$.

Figure 7:
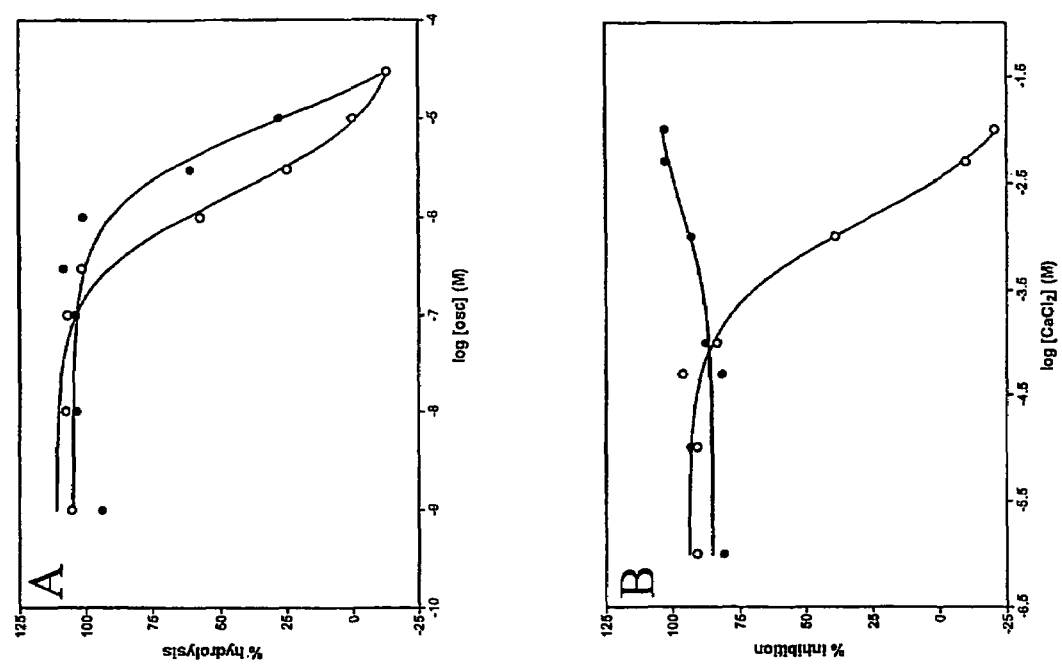

FIG. 7. Comparison of the effects of increasing concentrations of human-produced and E. coli-produced osteocalcin on PTHrP$_{107-139}$ degradation by purified secPHEX. (A) secPHEX activity was measured in the presence of increasing concentrations of human-produced (open symbols) or E. coli-produced (solid symbols) osteocalcin. 100% corresponds to the activity of secPHEX in the absence of osteocalcin. (B) osteocalcin inhibitory potency is measured and 100% corresponds to the inhibition observed in the presence of $2\times10^{-6}$M human-produced (open symbols) or E. coli-produced (solid symbols) osteocalcin and the absence of CaCl$_2$.

In order to provide a clear and consistent understanding of terms used in the present description, a number of definitions are provided hereinbelow.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

The nucleic acid (e.g. DNA or RNA) for practicing the present invention may be obtained according to well known methods.

The term "DNA" molecule or sequence (as well as sometimes the term "oligonucleotide") refers to a molecule comprised of the deoxyribonucleotides adenine (A), guanine (G), thymine (T) and/or cytosine (C), often in a double-stranded form, and comprises or includes a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction.

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^3$H, $^{14}$C, $^{32}$P, and $^{35}$S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. Patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press; 1990).

Ligase chain reaction (LCR) is carried out in accordance with known techniques (Weiss, 1991, Science 254:1292).

Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise to a specific polypeptide or protein. It will be readily recognized by the person of ordinary skill, that the nucleic acid sequence of the present invention can be incorporated into anyone of numerous established kit formats which are well known in the art.

A "heterologous" (e.g. a heterologous gene) region of a DNA molecule is a subsegment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked (or alternatively, "in frame") sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (e.g. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain −10 and −35 consensus sequences, which serve to initiate transcription and the transcript products contain Shine-Dalgarno sequences, which serve as ribosome binding sequences during translation initiation.

As used herein, the designation "functional derivative" denotes, in the context of a functional derivative of a sequence whether a nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include, similarities in charge, bulkiness, hydrophobicity, hydrophilicity and the like. The term "functional derivatives" is intended to include "fragments", "segments", "variants", "analogs" or "chemical derivatives" of the subject matter of the present invention.

Thus, the term "variant" refers herein to a protein or nucleic acid molecule which is substantially similar in structure and biological activity to the protein or nucleic acid of the present invention.

The functional derivatives of the present invention can be synthesized chemically or produced through recombinant DNA technology. All these methods are well known in the art.

As used herein, "chemical derivatives" is meant to cover additional chemical moieties not normally part of the subject matter of the invention. Such moieties could affect the physico-chemical characteristic of the derivative (e.g. solubility, absorption, half life, decrease of toxicity and the like). Such moieties are exemplified in Remington's Pharmaceutical Sciences (1980). Methods of coupling these chemical-physical moieties to a polypeptide or nucleic acid sequence are well known in the art.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in most other cellular components.

As used herein, the terms "molecule", "compound", "agent" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The agents can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modeling as mentioned above. Similarly, in a preferred embodiment, the polypeptides of the present invention are modified to enhance their stability and functionality. It should be understood that in most cases this modification should not alter the biological activity of the interaction domain. The molecules identified in accordance with the teachings of the present invention have a therapeutic value in diseases or conditions in which the physiology or homeostasis of the cell and/or tissue is compromised by a reduction in active PHEX. Alternatively, the molecules identified in accordance with the teachings of the present invention find utility in the development of increased PHEX activity.

As used herein, potentiators of PHEX results from the interaction of molecules where the PHEX activity is enhanced. In one embodiment, potentiators can be detected by contacting the indicator assay with a compound or mixture or library of molecules for a fixed period of time is then determined. An indicator assay in accordance with the present invention can be used to identify potentiators. For example, the test molecule or molecules are incubated with the host cell in conjunction with one or more molecules held at a fixed concentration. An indication and relative strength of the potentiating properties of the molecule(s) can be provided by comparing the level of peptide hydrolysis in the indicator assay in the presence of the agonist, in the absence of test molecules v. in the presence thereof. Of course, the potentiating effect of a molecule can also be determined in the absence of agonist, simply by comparing the level of hydrolysis product in the presence and absence of the test molecule(s).

It shall be understood that the "in vivo" experimental model can also be used to carry out an "in vitro" assay.

As exemplified herein below, the interaction domains of the present invention can be modified, for example by in vitro mutagenesis, to dissect the structure-function relationship thereof and permit a better design and identification of modulating compounds. However, some derivative or analogs having lost their biological function of interacting with their respective interaction partner may still find utility, for example for raising antibodies. Such analogs or derivatives could be used for example to raise antibodies to the interaction domains of the present invention. These antibodies could be used for detection or purification purposes. In addition, these antibodies could also act as competitive or non-competitive inhibitor and be found to be modulators of PHEX or osteocalcin interaction.

A host cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra). The use of a mammalian cell as indicator can provide the advantage of furnishing an intermediate factor, which permits for example the interaction of two polypeptides which are tested, that might not be present in lower eukaryotes or prokaryotes. Of course, such an advantage might be rendered moot if both polypeptide tested directly interact. It will be understood that extracts from mammalian cells for example could be used in certain embodiments, to compensate for the lack of certain factors.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody—A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents. Further, the DNA segments or proteins according to the present invention can be introduced into individuals in a number of ways. For example, erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (e.g. DNA construct, protein, cells), the response and condition of the patient as well as the severity of the disease.

Composition within the scope of the present invention should contain the active agent (e.g. fusion protein, nucleic acid, and molecule) in an amount effective to achieve the desired therapeutic effect while avoiding adverse side effects. Typically, the nucleic acids in accordance with the present invention can be administered to mammals (e.g. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

Materials and Methods

The production of the reagents used in the 201 method is summarised herein to enable a person skilled in the art to recognise useful improvements in this method.

DNA Manipulations

All DNA manipulations were performed according to standard protocols (19,20) (Ausubel et al., 1988; Sambrook et al., 1989)(Ausubel et al., 1988; Sambrook et al., 1989). Site-directed mutagenesis was performed using a PCR-based strategy as described previously (21).

Construction of Expression Vectors

Human PHEX cDNA was cloned previously (5). For expression of PHEX in cultured mammalian cells, a restriction fragment (SpeI-EcoRV), which contained the entire PHEX coding sequence, was digested, blunted, and subcloned into the mammalian expression vector pcDNA3/RSV (22). This vector also contains the bacterial neo gene that confers resistance to the antibiotic neomycin (G418) to cells that express it. The resulting vector, called pcDNA3/RSV-PHEX, encoded a membrane bound form of PHEX.

To obtain a soluble form of human PHEX, the signal peptide/membrane anchor domain (SA domain) of the protein was transformed into a cleavage-competent signal sequence following a strategy resembling that previously described to generate a soluble form of NEP (23). However, in the case of PHEX more genetic manipulations were needed. In addition to the strategy implemented for NEP, four codons had to be deleted in the SA domain of PHEX in addition to introducing hydrophilic amino acid residues. These modifications were achieved by introducing in vector pcDNA3/RSV/PHEX site-directed mutations (8 codons) and deletions (4 codons) by Polymerase Chain Reaction (PCR), using appropriate oligonucleotide primers, as described previously (21) (FIG. 1A).

Vector pcDNA3/RSV/secPHEXE581V which encodes an inactive secPHEX protein bearing the mutation Glu 581 to Val was obtained by site-directed mutagenesis using the same PCR-based strategy referred to above and appropriate oligonucleotide primers.

Vector PCDNA3/RSV/NL1-PHEX which encodes secPHEX fused with NL1, a furin cleavable signal peptide, was obtained by cloning in vector PCDNA3/RSV NL1 nucleotide sequence corresponding to amino acid residues 1 to 63 (15) (SEQ ID NO: 9)preceding and in frame with PHEX nucleotide sequence corresponding to amino acid residues 46 to 750 (5) (SEQ ID NO: 10).

A new Sequence Listing has been provided incorporating new sequences as requested by the Examiner, identified as SEQ ID NO: 9 to SEQ ID NO: 11.

To produce human osteocalcin in *E. coli*, total RNA was isolated from human osteoblast-like SaOS2 cells and osteocalcin sequences generated by RT-PCR using appropriate oligonucleotide primers. Osteocalcin sequence was verified by sequencing and introduced in pGEX vector (Amersham Pharmacia Biotech) to yield vector pGEX-OST.

Protein Production in *E. coli*

For production of osteocalcin in *E. coli*, pGEX-OST vector was introduced in bacterial strain AP401, and induction and purification of the protein performed as recommended by the supplier of the pGEX vector (Amersham Pharmacia Biotech).

Transfections and Cell Culture

Human PHEX, secPHEX and secPHEXE581V were expressed in LLC-$PK_1$ cells (Porcine Kidney cells; ATCC No. CRL-1392). To induce the stable expression of these recombinant proteins, appropriate vectors were transfected in LLC-$PK_1$ cells by the $CaPO_4$ precipitation method (24). Transfected cells were selected by adding 400 μg/ml G418 (Life Technologies, Burlington, ON, Canada) to the medium and cultured as described previously (25). Immunoblot analysis of PHEX-related proteins in cells and culture media For immunoblot analysis, confluent cell cultures were incubated for 16 h in DMEM medium (Life Technologies, Burlington, ON, Canada) containing 10 mM sodium butyrate to enhance expression of the cDNAs which are under the control of the RSV promoter. Cellular proteins were solubilized as previously described (26). Secreted proteins recovered in culture media were concentrated approximately 10 fold on Centriprep-50 columns (Amicon). Proteins (⅕₀th of the cellular proteins or of the proteins present in the culture medium from one petri dish) were resolved on 7.5% polyacrylamide/SDS gels and detected by immunobloting using a monoclonal antibody specific to human PHEX, as described previously (27).

To determine the glycosylation state of the proteins, samples were incubated prior to electrophoresis with endoglycosidase H (endoH) or peptide:N-glycosidase F (PNGaseF) as suggested by the distributor (New England Biolabs inc., Mississauga, ON, Canada).

Production of secPHEX or secPHEXE581V

To produce large amounts of secPHEX or secPHEXE581V, confluent cells were incubated for 4 days in 199 medium (Life Technologies, Burlington, ON, Canada) supplemented with 2.5 μg/ml insulin, 17.5 μg/ml transferrin, 2 μg/ml ethanolamine, 100 μg/ml soybean trypsin inhibitor and 10 μg/ml aprotinin. Sodium butyrate was present at a concentration of 10 mM. After 4 days, the media were recovered, centrifuged and concentrated on Centriprep-50 columns. Typically, 600 ml of crude spent medium from transfected LLC-$PK_1$ cells were concentrated to 30 ml before loading onto an ion-exchange column for purification.

Purification of secPHEX or secPHEXE581V

The concentrated medium was loaded, at a flow rate of 2 ml/min, on a 8 ml SP-Sepharose cation-exchange column (Amersham Pharmacia Biotech inc. Baie d'Urfée, QC, Canada) previously equilibrated with 50 mM sodium phosphate pH 6.6 containing 50 mM NaCl. The column was washed at the same flow rate with 10 column volumes of the same buffer and proteins eluted with a 50 mM to 1M NaCl gradient. Fractions were analyzed by SDS-PAGE and immunoblotted as described above, and fractions containing secPHEX or secPHEXE581V were visualized by silver staining.

Alternatively, and in preference to the 201 method, the following modifications in the purification method are recommended. Fractions containing secPHEX or secPHEXE581V are pooled and concentrated to approximately 1.5 mg/ml using Centriprep-50 columns. The protein solution is then diluted to 0.1 mg/ml with buffer A (50 mM phosphate pH 7.0 and 1 M ammonium sulfate), centrifuged at 9000 g for 15 min and loaded onto a 1 ml Butyl Sepharose 4 Fast Flow column (Amersham Pharmacia Biotech inc. Baie d'Urfée, QC, Canada) at a flow rate of 1 ml/min. The column is washed, at the same flow rate, with buffer A to a stable baseline and the proteins are eluted with a 40 ml gradient from 100% buffer A/0% buffer B (50 mM phosphate pH 7.0) to 0% buffer A/100% buffer B. Fractions are analyzed as described above and those containing secPHEX or secPHEXE581V are visualized by silver staining. Fractions containing pure secPHEX or secPHEXE581V are pooled, concentrated and dialyzed against 50 mM phosphate pH 6.5, 150 mM NaCl using Centriprep-50 columns. Protein concentrations are determined using the Bradford method (DC protein assay kit; Biorad, Mississauga, ON, Canada).

Enzymatic Assay

One µg of purified secPHEX or secPHEXE581V was incubated with 5 µg of peptide substrate for 30 min at 37° C. in a volume of 200 µl of 50 mM MES (2-(N-morpholino) ethanesulfonic acid) pH6.5, 150 mM NaCl. Peptide $PTHrP_{107-139}$ (human origin and obtained from Bachem, Philadelphia, Pa., U.S.A. or Peninsula Laboratories, Belmont, Calif., U.S.A.), used as a substrate, was prepared as 1 µg/µl solutions also containing 1 µg/µl of the tripeptide Tyr-Gly-Gly. This latter peptide, which is not a PHEX substrate, was used as an internal standard. Peptide substrate AWLDSGV (Dr Gilles Lajoie, Waterloo Peptide Synthesis C2-360 University of Waterloo, Waterloo, ON Canada) (SEQ ID NO: 1) was digested with secPHEX in the same manner as described above for $PTHrP_{107-139}$. To determine osteocalcin inhibitory potency on secPHEX activity, osteocalcin (Peptide Research Institute, Japan or E. coli-produced) was added to the reaction mixture to final concentrations varying from $10^{-8}$ to $5 \times 10^{-4}$ M. To determine the effect of agents on the inhibitory activity of osteocalcin, the agents were added to a reaction mixture containing secPHEX, peptide substrate and $5 \times 10^{-6}$ M osteocalcin. This concentration of osteocalcin yields approximately 75% inhibition of secPHEX activity. Following the incubation period, hydrolysis was stopped by the addition of EDTA to a final concentration of 5 mM. The potentiating agent was identified when the intact substrate was determined to be present in a lower concentration than in the absence of the potentiating agent (see FIG. 6). Results were quantified by comparing, after normalization for the amounts of peptide Tyr-Gly-Gly present in the samples, the areas under the peaks of the substrate.

Identification and quantification of the enzymatic activity of secPHEX on the $PTHrP_{107-139}$ peptide was performed by reverse phase high performance liquid chromatography (RP-HPLC) on a C18 µBondapak analytical column (Waters, Mississauga, ON, Canada) with a UV detector set at 214 nm. Peptides were resolved with a linear gradient of 5% B to 85% B in 45 min at the flow rate of 0.4 ml/min [mobile phase A=0.1% trifluoroacetic acid; mobile phase B=80% acetonitrile ($CH_3CN$), 0.1% trifluoroacetic acid].

Identification and quantification of the enzymatic action of PHEX on the AWLDSGV peptide (SEQ ID NO: 1) was performed by reverse phase high performance liquid chromatography (RP-HPLC) on a 5 µm ZORBAX 300SB-C18 analytical column (Agilent Technologies, Mississauga, ON, Canada) maintained at 40° C. with a UV detector set at 220 nm. Peptides were resolved with a linear gradient of 30% B to 45% B in 10 min at the flow rate of 1,0 ml/min [mobile phase A=0.1% trifluoroacetic acid; mobile phase B=80% acetonitrile ($CH_3CN$), 0.1% trifluoroacetic acid].

The secPHEX digestion products of $PTHrP_{107-139}$ were characterized by mass spectrometry (MALDI Tof) at the McGill University Mass Spectrometry Center.

Administration of secPHEX

Purified secPHEX solubilized in 1 mM phosphate pH 7.4, 150 mM NaCl, was administered intravenously daily for 4 or 14 consecutive days through the subclavian vein Hyp males (12 weeks of age). The same number of aged-matched Hyp male mice were treated with vehicle only as controls.

Results

Construction and Expression of a Soluble Form of PHEX

Figure 1:
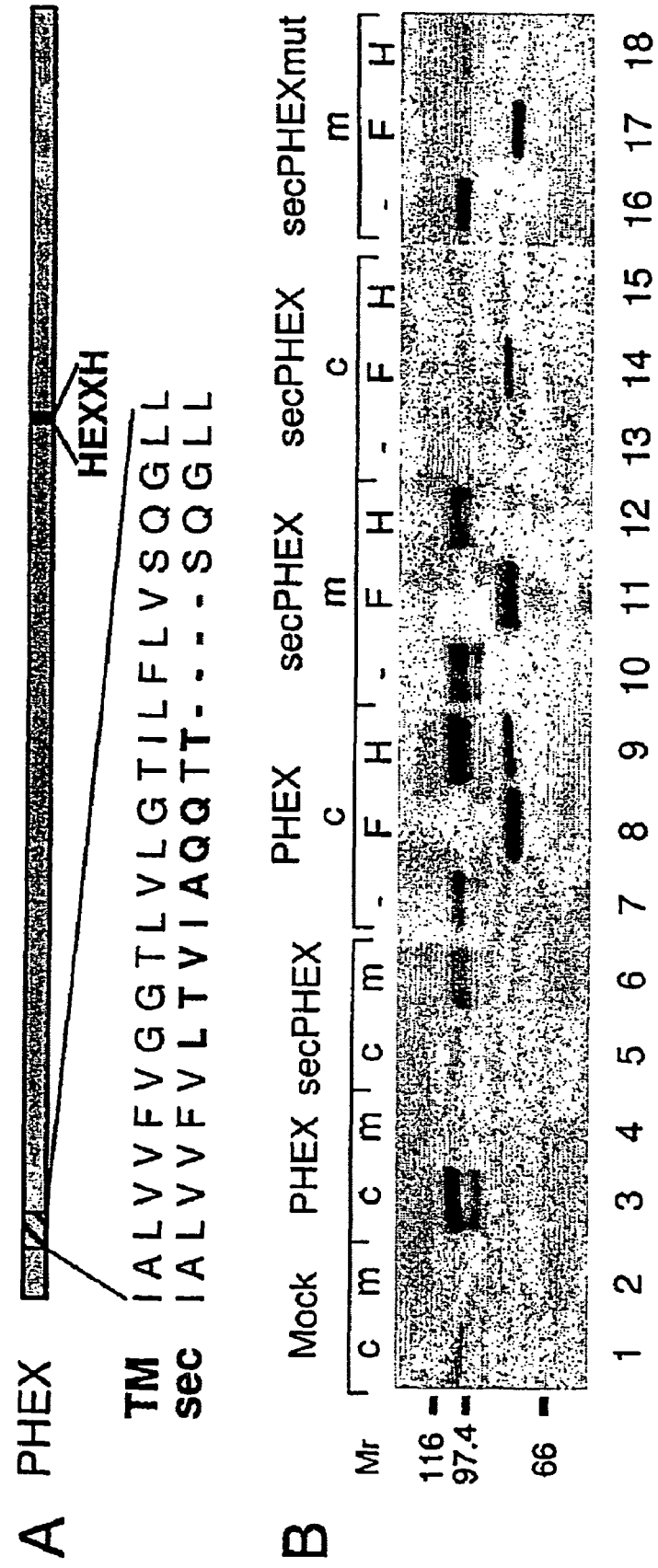
FIG. 1. Structure and expression of PHEX, secPHEX and secPHEXE581V.

To obtain a soluble form of recombinant human PHEX, we first attempted to transform the signal peptide/transmembrane anchor (SA) domain of PHEX into a cleavage-competent signal peptide using the strategy described previously to generate a soluble form of NEP (23). This strategy resulted in the production of a misfolded PHEX protein that remained trapped in the rough endoplasmic reticulum of transfected cells (results not shown). Therefore, an alternate strategy was developed which consisted in the deletion of selected amino acids in the SA domain of PHEX in addition to substitution of hydrophilic amino acid residues for hydrophobic ones (FIG. 1A).

LLC-$PK_1$ cells were transfected with pcDNA3/RSV expression vectors containing cDNAs for the membrane or soluble forms of PHEX, and permanent cell lines were established as described under Materials and Methods (LLC-$PK_1$/PHEX and LLC-$PK_1$/secPHEX cells, respectively, for the membrane-bound and soluble forms). Immunoblotting with a PHEX-specific monoclonal antibody (27) of extracts of LLC-$PK_1$/PHEX cells revealed a major band of 105 kDa and a minor band of 95 kDa (FIG. 1B, lane 3). No protein was found in the culture medium, as expected for an integral membrane protein (FIG. 1B, lane 4). In contrast, secPHEX appeared in the culture medium as a 100 kDa species (FIG. 1B, lane 6) with very little enzyme in the cell extract (FIG. 1B, lane 5). To characterize the glycosylation state of PHEX and secPHEX, we next submitted the recombinant proteins to deglycosylation by peptide:N-glycosidase F (PNGase F) and endoglycosidase H (endo H). PNGase F removes high mannose as well as most complex N-linked oligosaccharides added in the Golgi complex. In contrast, endo H removes N-linked oligosaccharide side chains of the high mannose type found on proteins in the RER but which have not yet transited through the Golgi complex; thus, resistance to endo H can be used as an indication that the protein has traveled through the Golgi complex. PNGase F treatment showed that all PHEX and secPHEX species were N-glycosylated as their electrophoretic mobility increased following digestion (FIG. 1B, compare lanes 7 and 8, 10 and 11, 13 and 14). Treatment of PHEX with endo H resulted in faster migration of the 95 kDa band (FIG. 1B, lane 9), indicating that this PHEX species is probably an underglycosylated RER-associated form. The major 105 kDa band was resistant to endo H digestion (FIG. 1B, lane 9), consistent with a cell-surface expression of the enzyme as was previously shown for a tagged-form of PHEX (7). secPHEX present in the culture medium was also resistant to endo H digestion (FIG. 1B, lane 12), suggesting true secretion of the enzyme. In contrast, secPHEX from cell extract was sensitive to endo H treatment (FIG. 1B, lane 15). The results show differences in the glycosylation state of secPHEX from the culture medium and the cellular extract, and suggests that the cell-associated form of secPHEX is an intracellular species that has not traveled through the Golgi complex.

NL1 is a peptidase secreted by cells due to a furin-cleavage site in its extracellular domain (15). We have taken advantage of this feature of NL1 to construct a fusion protein formed of NL1 N-terminal region (up to and including the furin-cleavage site (see 42)) and PHEX extracellular domain. Vector PCDNA3/RSV/NL1-PHEX also promoted the secretion of a soluble form of PHEX (Western blot not shown). The advantage of this method over the previous one described above is the possibility to have fewer foreign amino acid residues in N-terminus of secPHEX that could elicit an immunological response.

Purification of secPHEX

SecPHEX could be purified to homogeneity using a two-step procedure (FIG. 2). First, the concentrated culture medium (FIG. 2, lane 1) was loaded onto a SP-Sepharose column and the proteins eluted with a 0.05 to 1 M NaCl gradient. secPHEX eluted at 150-200 mM NaCl. We estimated the amount of secPHEX recovered after this first step at about 2 mg per liter of culture. One contaminant protein eluted with secPHEX (FIG. 2, lane 2). This contaminant protein was separated from secPHEX on the Butyl Sepharose 4 column (FIG. 2, lane 3). The final yield of the purification procedure was estimated at approximately 1 mg of purified secPHEX per liter of culture.

Activity of secPHEX

SecPHEX activity was assayed in 50 mM MES pH 6.5 containing 150 mM NaCl (26). Sodium chloride was added to the reaction mixture because we observed that secPHEX precipitated out in solutions containing less than 50 mM salt.

In the absence of secPHEX, no digestion of $PTHrP_{107-139}$ (SEQ ID NO: 4) (elution time 31.5 min) was evident (FIG. 3A). In the presence of secPHEX, however, approximately 75 to 80% degradation of the peptide was observed (FIG. 3B). (The peak eluting at 7 min corresponds to Tyr-Gly-Gly used as internal standard). Digestion of $PTHrP_{107-139}$ by secPHEX resulted in the production of four degradation products eluting at 23.5, 24.2, 27.0 and 29.4 min (FIG. 3B). As expected for a zinc metallopeptidase, secPHEX activity was fully inhibited by the addition of 1 mM EDTA (FIG. 3C) or 1 mM 1,10-phenanthroline (result not shown) to the reaction mixture.

To confirm that the activity of secPHEX was not due to a contaminant protease co-purifying with it, a mutant of secPHEX, secPHEXE581V, in which the critical catalytic $Glu_{581}$ was replaced by a Val residue, was constructed. A similar mutation introduced in NEP (28) or ECE-1 (29) resulted in total loss of catalytic activity. secPHEXE581V was produced in LLC-PK$_6$ cells and showed an expression pattern essentially identical to that of secPHEX (FIG. 1B, compare lanes 10, 11 and 12 with lanes 16, 17 and 18, respectively). However, in contrast to the wild-type form of the secreted enzyme, purified secPHEXE581V failed to degrade $PTHrP_{107-139}$ under similar conditions (FIG. 3D).

PHEX Selectivity

To determine the cleavage site specificity of secPHEX, reverse-phase HPLC peaks corresponding to the degradation products of $PTHrP_{107-139}$ were collected and analyzed by mass spectrometry (MALDI-Tof). FIG. 4 depicts the $PTHrP_{107-139}$ fragments identified (SEQ ID NO: 5 to SEQ ID NO: 8). As can be seen from the cleavage sites identified, hydrolysis of the peptide by secPHEX occurred at the amino-terminus of aspartate residues.

The pH optimum for the reaction was determined by progressively increasing the pH of the MES buffer from 5.0 to 7.0 or of a Tris buffer (50 mM Tris.HCl, 150 mM NaCl) from 7.0 to 9.0. Maximum activity was observed at pH 6.5 (FIG. 5). secPHEX activity rapidly decreased at more basic pH values.

Inhibition of secPHEX Activity

In previous studies we noticed that NEP activity was sensitive to the presence of Pi in the incubation medium (unpublished results). To determine whether secPHEX had the same sensitivity to Pi, we examined the effect of Pi, from 0.1 to 50 mM, on secPHEX activity and found that 50% inhibition was achieved by 3.5 mM Pi. Since Pi proved to be an effective inhibitor of secPHEX and since pyrophosphate, an alkaline phosphatase substrate, is abundant in bone (41), we also examined its effect on secPHEX activity. Increasing the pyrophosphate concentration from 0.1 to 50 mM demonstrated that 50% inhibition of enzyme activity was achieved at 2.5 mM (FIG. 6A).

secPHEX specificity for aspartate residues (FIG. 4) suggested that the $S_1'$ pocket can accommodate negatively charged side chains of amino acid residues. Although osteocalcin, which contains 3 negatively-charged y-carboxy glutamic acid residues (Gla), was not degraded by secPHEX (data not shown), it was a potent inhibitor of secPHEX-mediated $PTHrP_{107-139}$ hydrolysis. Fifty percent inhibition of secPHEX activity was achieved at $3.6 \times 10^{-6}$ M osteocalcin (FIG. 6A).

Restoration of PHEX Activity

The Gla residues of osteocalcin are known to bind calcium ions (30). We thus examined the effect of $Ca^{2+}$ on the inhibitory action of osteocalcin. By varying the $CaCl_2$ concentration in the assay from $10^{-6}$ to $10^{-2}$ M, we showed that $5 \times 10^{-3}$ M $Ca^{2+}$ was necessary to reduce the inhibitory potency of osteocalcin by 50% (FIG. 6B). $Ca^{2+}$ had no effect on secPHEX activity in the absence of osteocalcin (data not shown).

The mechanisms by which osteocalcin and inorganic pyrophosphate function as PHEX inhibitors are still unknown. However, both molecules have negatively charged chemical groups (Gla residues in osteocalcin and phosphate groups in pyrophosphate) that may interact in the same fashion with the enzyme. The observation that $Ca^{2+}$ can prevent PHEX inhibition by osteocalcin suggests the hypothesis that Gla residues are involved in osteocalcin/PHEX interaction. Indeed, it has been shown that vitamin K-dependent y-carboxylation of osteocalcin glutamic acid residues 17, 21 and 24 is required for $Ca^{2+}$ binding (31). Atkinson et al (40) have shown that $Ca^{2+}$ binding to Gla residues induces a conformational change which may be responsible for the restoration of PHEX activity. To test this hypothesis, human osteocalcin without Gla residues was made in E. coli and its inhibitory potency in the absence or presence of $Ca^{2+}$ compared to that of osteocalcin extracted from human bones (with Gla residues). E. coli-produced osteocalcin has an inhibitory potency similar to osteocalcin extracted from bones (FIG. 7A) but its activity was not modulated by $Ca^{2+}$ (FIG. 7B). These observations indicate that the Gla residues are not essential for osteocalcin/PHEX interaction but are important for the calcium-induced conformational change of the molecule that results in its inability to inhibit PHEX.

secPHEX Injection to Hyp Mice

Daily injection of purified secPHEX over 4 days to Hyp male mice significantly (Student t test p<0.05) decreased serum phosphate as a function of dose (see table 1). Hyp mouse and XLH patient have an already low serum phosphate and low bone mass. Our results demonstrate that upon secPHEX administration serum levels are further reduced. This result is consistent with the concept of "hungry bones" where the available phosphate is mobilized from the serum to undermineralized bones.

TABLE 1

Dose response of secPHEX on serum phosphate

| Day 0 | Day 4 | Dose (mg/kg) |
|---|---|---|
| 1.26 | 1.29 | 0 |
| 0.99 | 1.14 | 0 |
| 1.26 | 1.22 | 0 |
| 1.36 | 1.18 | 1 |
| 1.37 | 1.31 | 1 |
| 1.68 | 1.23 | 1 |
| 1.25 | 1.06 | 1 |
| 1.16 | 0.92 | 10 |
| 1.12 | 0.82 | 10 |
| 1.39 | 0.89 | 10 |
| 1.14 | 0.87 | 10 |

In a similar experiment, Hyp male mice where injected with daily doses of 1 mg/kg secPHEX for 14 days. In this experiment, the serum alkaline phosphatase levels were significantly reduced toward normal levels (71+/−11 units) (see Table 2, Student t test $p<0.05$), indicating a process of normalization of the physiological status of the bones.

TABLE 2

Alkaline phosphate level at 7 day pre-treatment and after 7 and 14 of daily sec PHEX injection

|  | Pre-treatment | $7^{th}$ day of treatment | $14^{th}$ day of treatment |
|---|---|---|---|
| Control | 448 | 309 | 247 |
| Control | 445 | 317 | 276 |
| Control | 373 | 235 | 232 |
| Control | 283 | 187 | 198 |
| Control | 286 | 290 | 257 |
| 1 mg/kg sec PHEX | 292 | 183 | 196 |
| 1 mg/kg sec PHEX | 357 | 235 | 196 |
| 1 mg/kg sec PHEX | 377 | 233 | 208 |
| 1 mg/kg sec PHEX | 348 | 199 | 193 |
| 1 mg/kg sec PHEX | 323 | 246 | 218 |

At the same time serum phosphate levels where monitored and found to be at the same level as pretreatment at the $7^{th}$ and $14^{th}$ day. This information in combination with the 4 day experiment above, indicates that upon secPHEX administration phosphate levels are first reduced due to the "hungry bone" effect, followed by a slow increase toward normal levels. This time-dependent process of normalization presented here is consistent with the general knowledge that bone healing occurs over long periods of time.

These results confirm that secPHEX can be used to improve conditions in mammals related to low bone mass, including the management of X-linked hypophosphatemia and osteoporosis as well as for patients requiring osteogenesis resulting from orthopedic or dental interventions.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

LIST OF REFERENCES

1. The HYP Consortium (1995). Nature Genet 11:130-136.
2. Rasmussen H., Tenenhouse H S (1995). In: The Metabolic and Molecular Basis of Inherited Disease. Scriver C R, Beaudet A L, Sly W S, Valle D, editors. McGraw Hill Book Co, New York, 3717-3745.
3. Du L, Desbarats M, Viel J, Glorieux F H, Cawthorn C, Ecarot B (1996). Gemonics 36:22-28.
4. Grieff M, Mumm S, Waeltz P, Mazzarella R, Whyte M P, Thakker R V, Schlessinger D (1997). Biochem Biophys Res Commun 231:635-639.
5. Beck L, Soumounou Y, Martel J, Krishnamurthy G, Gauthier C, Goodyer C G, Tenenhouse H S (1997). J Clin Invest 99:1200-1209.
6. Guo R, Quarles L D (1997). J Bone Miner Res 12:1009-1017.
7. Lipman M L, Panda D, Bennett H P J, Henderson J E, Shane E, Shen Y, Goltzman D, Karaplis A C (1998). J Biol Chem 273:13729-13737.
8. Crine P, Dion N, Boileau G (1997). In: Cell-surface peptidases in health and disease (Kenny A J and Boustead C M, eds) pp. 79-98, BIOS Scientific Publishers Ltd., Oxford, UK.
9. Roques B P, Noble F, Dauge V, Fournie-Zaluski M C, Beaumont A (1993). Pharmacol. Rev. 45, 87-146.
10. Turner, A J (1997). In: Cell-surface peptidases in health and disease (Kenny A J and Boustead C M, eds) pp. 137-153, BIOS Scientific Publishers Ltd., Oxford, UK.
11. Marsh W L (1992) Transfusion 32, 98-101.
12. Valdenaire O, Rohrbacher E, Langeveld A, Schweizer A, Meijers C (2000). Biochem. J. 346, 611-616.
13. Kiryu-Seo S, Sasaki M, Yokohama H, Nakagomi S, Hirayama T, Aoki S, Wada K, Kiyama H (2000). Proc. Natl. Acad. Sci. USA 97, 4345-4350.
14. Ikeda, K., Emoto, N., Raharjo, S. B., Nurhantari, Y., Saiki, K., Yokoyama, M., Matsuo, M. (1999). J. Biol. Chem. 274, 32469-32477.
15. Ghaddar G, Ruchon A F, Carpentier M, Marcinkiewicz M, Seidah N G, Crine P, DesGroseillers L, Boileau G (2000). Biochem. J. 347, 419-429.
16. Lajeunesse D, Meyer R A Jr, Hamel L (1996). Kidney Int. 50, 1531-1538.
17. Nesbitt T, Fujiwara I, Thomas R, Xiao Z S, Quarles L D, Drezner M K (1999). J. Bone Miner. Res. 14, 2027-2035.
18. Tenenhouse H S (1999) Nephrol. Dial. Transplant. 14, 333-341.
19. Ausubel F M, Brent R, Kingston R E, Moore D D, Smith J A (1988) Current Protocoles in Molecular Biology, Wiley Interscience, New York.
20. Sambrook J, Fritsch E F, Maniatis T (1989) Molecular Cloning: A Laboratory Manual, Cold Spring Harbor Laboratory Press, Cold Spring Harbor, N.Y.
21. Le Moual H., Dion N., Roques B P, Crine P, Boileau G (1994) Eur. J. Biochem. 221, 475480.
22. Jockers R, Da Silva A, Strosberg A D, Bouvier M, Marullo S (1996) J. Biol. Chem. 271, 9355-9362.
23. Lemire I, Lazure C, Crine P, Boileau G (1997) Biochem. J. 322, 335-342.
24. Chen C, Okayama H (1987) Mol. Cell Biol. 7, 2745-2752.
25. Lanctôt C, Fournier H, Howell S, Boileau G, Crine P (1995) Biochem. J. 305, 165-171.
26. Dion N, Le Moual H, Fournie-Zaluski M C, Roques B P, Crine P, Boileau G (1995) Biochem. J. 311, 623-627.

27. Ruchon A F, Tenenhouse H S, Marcinkiewicz M, Siegfried G, Aubin J E, DesGroseillers L, Crine P, Boileau G (2000) J. Bone Miner. Res. 15, 1440-1450.
28. Devault A, Nault C, Zollinger M, Fournie-Zaluski M-C, Roques B P, Crine P, Boileau G (1988) J. Biol. Chem. 263, 40334040.
29. Shimada K, Takahashi M, Turner A J, Tanzawa K (1996) Biochem. J. 315, 863-867.
30. Moss D W, Eaton R H, Smith J K, Withby L G (1967) Biochem. J. 102, 53-57.
31. Poser J W, Price P A (1979) J. Biol. Chem. 254, 6291-6298.
32. Ruchon A F, Marcinkiewicz M, Siegfried G, Tenenhouse H S, DesGroseillers L, Crine P, Boileau G (1998) J. Histochem. Cytochem. 46, 1-10.
33. Marie P J, Travers R, Glorieux F H (1981) J. Clin. Invest. 67, 911-914.
34. Van der Rest M, de Miguel E, Glorieux F H (1981) Calcif. Tissue Int. 33, 77-79.
35. Delvin E E, Richard P, Desbarats M, Ecarot-Charrier B, Glorieux F H (1990) Bone 11, 87-94.
36. Romberg R W, Werness P G, Riggs B L, Mann K G (1986) Biochemistry, 25, 1176-1180.
37. Van de Loo P G, Soute B A, van Haarlem L J, Vermeer C (1987) Biochem. Biophys. Res. Commun. 142, 113-119.
38. Ducy P, Desbois C, Boyce B, Pinero G, Story B, Dunstan C, Smith E, Bonadio J, Goldstein S, Gundberg C, Bradley A, Karsenty G (1996) Nature 382, 448-452.
39. Lian J B, Stein G S, Canalis E, Robey P G, Boskey A I, in Primer on the metabolic bone disease and disorder of mineral metabolism, Favus M J ed, $4^{th}$ ed, An official publication of the American Society for Bone and Mineral Research, Lippincot Williams & Wilkins publisher, p14-29)
40. Atkinson R. A., Evans J. S., Hauschka P. V. Levine B. A., Meats R., Triffit J. T., Virdi A. S., Williams R. P. J., (1995) Eur. J. Biochem. 232, 515-521.
41. Whyte M P (1994) Endocrine Rev. 15, 439-461.
42. Bergeron F, Leduc R, Day R (2000) J Mol Endocrinol. Feb; 24(1):1-22. Review.

---

The invention claimed is:

1. A method of treating a bone-related disorder requiring osteogenesis in a mammal, or treating a condition requiring osteogenesis in a mammal, comprising administering an effective amount of a soluble Phosphate Regulating Gene With Homologies To Endopeptidases On The X Chromosome protein (secPHEX) that comprises the sequence of amino acids as set forth in SEQ ID NO:11.

2. The method as recited in claim 1, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 and a cleavage-competent signal sequence that is substituted for the wild-type signal peptide/membrane anchor domain of a PHEX protein.

3. The method as recited in claim 1, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 fused at its amino terminus to the amino acid sequence set forth in SEQ ID NO:3.

4. The method as defined in claim 1, wherein said bone-related disorder requiring osteogenesis is selected from the group consisting of osteopenia, osteoporosis, rickets, and X-linked hypophosphatemic rickets (XLH), and wherein said condition requiring osteogenesis is an orthopedic intervention and or a dental intervention.

5. The method as recited in claim 4, wherein said bone-related disorder is XLH.

6. The method as recited in claim 5, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 and a cleavage-competent signal sequence that is substituted for the wild-type signal peptide/membrane anchor domain of a PHEX protein.

7. The method as recited in claim 5, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 fused at its amino terminus to the amino acid sequence set forth in SEQ ID NO:3.

8. A composition for treating a bone-related disorder requiring osteogenesis in a mammal, or treating a condition requiring osteogenesis in a mammal comprising an effective amount of a soluble Phosphate Regulating Gene With Homologies To Endopeptidases On The X Chromosome protein (secPHEX) and a pharmaceutically-acceptable carrier, wherein the secPHEX protein comprises the sequence of amino acids as set forth in SEQ ID NO:11.

9. The composition as recited in claim 8, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 and a cleavage-competent signal sequence that is substituted for the wild-type signal peptide/membrane anchor domain of a PHEX protein.

10. The composition as recited in claim 8, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 fused at its amino terminus to the amino acid sequence set forth in SEQ ID NO:3.

11. An orthopedic implant comprising a soluble Phosphate Regulating Gene With Homologies To Endopeptidases On The X Chromosome protein (secPHEX) protein that comprises the sequence of amino acids as set forth in SEQ ID NO:11.

12. The orthopedic implant as recited in claim 11, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 and a cleavage-competent signal sequence that is substituted for the wild-type signal peptide/membrane anchor domain of a PHEX protein.

13. The orthopedic implant as recited in claim 11, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 fused at its amino terminus to the amino acid sequence set forth in SEQ ID NO:3.

14. A dental prosthesis comprising a soluble Phosphate Regulating Gene With Homologies To Endopeptidases On The X Chromosome protein (secPHEX) protein that comprises the sequence of amino acids as set forth in SEQ ID NO:11.

15. The dental prosthesis as recited in claim 14, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 and a cleavage-competent signal sequence that is substituted for the wild-type signal peptide/membrane anchor domain of a PHEX protein.

16. The dental prosthesis as recited in claim 14, wherein the secPHEX protein is obtained by the recombinant expression within an isolated host cell of a vector comprising a nucleotide sequence encoding a fusion polypeptide comprising a secPHEX protein having the amino acid sequence set forth in SEQ ID NO:11 fused at its amino terminus to the amino acid sequence set forth in SEQ ID NO:3.

17. A method of producing a soluble Phosphate Regulating Gene With Homologies To Endopeptidases On The X Chromosome protein (secPHEX) comprising expressing an in frame fusion of a nucleotide sequence encoding the amino acid sequence from position 1 through position 63 of Neprilysin-Like peptidase (NL1) as set forth in SEQ ID NO:9 with a nucleotide sequence encoding the amino acid sequence set forth in SEQ ID NO:11.

18. A vector comprising an in frame fusion of a nucleotide sequence encoding the amino acid sequence from position 1 through position 63 of Neprilysin-Like peptidase (NL1) as set forth in SEQ ID NO:9 with a nucleotide sequence encoding the amino acid sequence set forth in SEQ ID NO:11.

19. A method of expressing a soluble Phosphate Regulating Gene With Homologies To Endopeptidases On The X Chromosome protein (secPHEX) in an isolated host cell comprising:
  (i) providing an expression vector comprising an in frame fusion of a nucleotide sequence encoding the amino acid sequence from position 1 through position 63 of Neprilysin-Like peptidase (NL1) set forth in SEQ ID NO:9 with a nucleotide sequence encoding the amino acid sequence set forth in SEQ ID NO:11;
  (ii) introducing the vector into an isolated host cell; and
  (iii) maintaining the isolated host cell under conditions permitting expression of secPHEX protein in the cell.

20. A method of separating a soluble Phosphate Regulating Gene With Homologies To Endopeptidases On The X Chromosome protein (secPHEX) from other components in a solution by applying the solution to a hydrophobic chromatographic column and removing those fractions comprising the secPHEX protein, wherein the secPHEX protein comprises the sequence of amino acids as set forth in SEQ ID NO:11, thereby separating the secPHEX protein from other components of the solution.

21. A method of separating a soluble Phosphate Regulating Gene With Homologies To Endopeptidases On The X Chromosome protein (secPHEX) from other components in a solution by applying the solution to an ion-exchange chromatographic column and removing those fractions comprising the secPHEX protein, wherein the secPHEX protein comprises the sequence of amino acids as set forth in SEQ ID NO:11, thereby separating the secPHEX protein from other components of the solution. fused at its amino terminus to the amino acid sequence set forth in SEQ ID NO:3.

22. A secPHEX fusion polypeptide encoded by the vector of claim 18.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: Homo sapiens

<400> SEQUENCE: 1

Ala Trp Leu Asp Ser Gly Val
 1               5

<210> SEQ ID NO 2
<211> LENGTH: 25
<212> TYPE: PRT
<213> ORGANISM: Homo sapiens

<400> SEQUENCE: 2

Ile Ala Leu Val Val Phe Val Gly Gly Thr Leu Val Leu Gly Thr Ile
 1               5                  10                  15

Leu Phe Leu Val Ser Gln Gly Leu Leu
            20                  25

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Mutated Sec
      PHEX transmembrane domain

<400> SEQUENCE: 3

Ile Ala Leu Val Val Phe Val Leu Thr Val Ile Ala Gln Gln Thr Thr
 1               5                  10                  15

Ser Gln Gly Leu Leu
            20

<210> SEQ ID NO 4
<211> LENGTH: 33
<212> TYPE: PRT
<213> ORGANISM: Homo sapiens
```

```
-continued

<400> SEQUENCE: 4

Thr Arg Ser Ala Trp Leu Asp Ser Gly Val Thr Gly Ser Gly Leu Glu
  1               5                  10                  15

Gly Asp His Leu Ser Asp Thr Ser Thr Thr Ser Leu Glu Leu Asp Ser
             20                  25                  30

Arg

<210> SEQ ID NO 5
<211> LENGTH: 6
<212> TYPE: PRT
<213> ORGANISM: Homo sapiens

<400> SEQUENCE: 5

Thr Arg Ser Ala Trp Leu
  1               5

<210> SEQ ID NO 6
<211> LENGTH: 21
<212> TYPE: PRT
<213> ORGANISM: Homo sapiens

<400> SEQUENCE: 6

Thr Arg Ser Ala Trp Leu Asp Ser Gly Val Thr Gly Ser Gly Leu Glu
  1               5                  10                  15

Gly Asp His Leu Ser
             20

<210> SEQ ID NO 7
<211> LENGTH: 9
<212> TYPE: PRT
<213> ORGANISM: Homo sapiens

<400> SEQUENCE: 7

Asp Thr Ser Thr Thr Ser Leu Glu Leu
  1               5

<210> SEQ ID NO 8
<211> LENGTH: 12
<212> TYPE: PRT
<213> ORGANISM: Homo sapiens

<400> SEQUENCE: 8

Asp Thr Ser Thr Thr Ser Leu Glu Leu Asp Ser Arg
  1               5                  10
```